United States Patent [19]

Michaels

[11] Patent Number: 5,051,236

[45] Date of Patent: Sep. 24, 1991

[54] PROCESS FOR REDUCING THE CONCENTRATION OF VIABLE CELLS IN A FLOWABLE FLUID

[75] Inventor: Alan S. Michaels, Chestnut Hill, Mass.

[73] Assignee: FMC Corporation, Philadelphia, Pa.

[21] Appl. No.: 286,564

[22] Filed: Dec. 19, 1988

[51] Int. Cl.$^5$ .............................................. A23L 3/34
[52] U.S. Cl. ............................................ 422/1; 422/28; 422/30; 422/32; 426/271; 426/330; 426/330.5; 426/489; 426/495; 426/521; 426/590; 426/599
[58] Field of Search ................. 422/1, 28, 30, 32; 426/271, 330, 330.5, 330.3, 489, 495, 521, 590, 599

[56] References Cited

U.S. PATENT DOCUMENTS

| | | | |
|---|---|---|---|
| 512,133 | 1/1894 | Vander Weyde et al. | |
| 751,179 | 2/1904 | Kollrepp et al. | |
| 1,256,758 | 2/1918 | Williams | |
| 1,915,568 | 8/1928 | Gortner et al. | |
| 1,972,561 | 3/1932 | Heubaum | 204/1 |
| 2,089,116 | 8/1937 | Dyckerhoff | 99/69 |
| 2,159,074 | 5/1939 | Briggs | 204/34 |
| 2,631,100 | 3/1953 | Aten et al. | 99/57 |
| 2,671,055 | 3/1954 | Aten et al. | 204/131 |
| 2,688,572 | 9/1954 | Warshaw | 127/54 |
| 2,830,905 | 4/1958 | Block et al. | 99/54 |
| 3,165,415 | 1/1965 | Kilburn et al. | 99/105 |
| 3,201,245 | 8/1965 | Clark et al. | 99/57 |
| 3,290,173 | 12/1966 | Marino | 127/63 |
| 3,369,906 | 2/1968 | Chen | 99/77 |
| 3,433,726 | 3/1969 | Parsi et al. | 204/180 |
| 3,447,930 | 6/1969 | Francis | 99/57 |
| 3,475,216 | 10/1969 | Walon | 127/46 |
| 3,547,657 | 12/1970 | Otsuka et al. | 99/111 |
| 3,666,647 | 5/1972 | Kubo et al. | 204/180 P |
| 3,687,682 | 8/1972 | Scheder | 99/57 |
| 3,709,802 | 1/1973 | Okuhara et al. | 204/137 R |
| 3,781,174 | 12/1973 | Nishijima et al. | 127/46 A |
| 3,845,226 | 10/1974 | Goujard | 426/239 |
| 3,865,960 | 2/1975 | Wucherpfennig et al. | 426/239 |
| 3,968,017 | 7/1976 | Canata et al. | 204/180 P |
| 4,138,501 | 2/1979 | Chaveron et al. | 426/329 |
| 4,160,713 | 7/1979 | Matsuzaki et al. | 204/180 P |
| 4,212,891 | 7/1980 | Fujita et al. | 426/321 |
| 4,264,631 | 4/1981 | Rose | 426/247 |
| 4,317,841 | 3/1982 | Brambilla et al. | 426/329 |
| 4,322,448 | 3/1982 | Matsuura et al. | 426/490 |
| 4,374,714 | 2/1983 | Hekal | 204/131 |
| 4,401,678 | 8/1983 | Beaumont | 426/15 |
| 4,492,601 | 1/1985 | Nakasone et al. | 127/48 |
| 4,523,959 | 6/1985 | Exertier | 127/46 |
| 4,539,212 | 9/1985 | Hunter | 426/123 |
| 4,643,902 | 2/1987 | Lawhon et al. | 426/271 |
| 4,670,125 | 6/1987 | Mueller et al. | 204/296 |
| 4,766,161 | 8/1988 | Chlanda et al. | 521/27 |

OTHER PUBLICATIONS

Fennema, "Principles of Food Science", Food Chemistry, Part I, Marcel Dekker, Inc., New York, 1976, pp. 466-467.

Primary Examiner—Robert J. Warden
Assistant Examiner—Timothy M. McMahon
Attorney, Agent, or Firm—E. R. Elden; A. J. Moore

[57] ABSTRACT

A process is provided for sterilizing or pasturizing aqueous fluids by contacting the aqueous fluid with a permeable membrane to separate the fluid into a serum and a residue, separating the serum into two portions, the pH of the first portion is increased and the pH of the second is decreased. The second portion of serum is combined with the residue, maintained at an elevated temperature to reduce the concentration of microbial cells, and combined with the first portion of serum to reconstitute the flowable fluid with a reduced concentration of viable cells.

18 Claims, 1 Drawing Sheet

PROCESS FOR REDUCING THE CONCENTRATION OF VIABLE CELLS IN A FLOWABLE FLUID

A process is provided for reducing the concentration of viable microbial cells in a flowable fluid by separating the flowable fluid into a sterile, colloid-free serum and a residue, decreasing the pH of part of the serum, combining said part with residue and heating to reduce the concentration of viable microbial cells in the combined mixture concomitantly increasing the pH of the balance of the serum and incorporating it into the combined mixture thereby reconstituting the flowable fluid with a reduced concentration of viable cells.

Acidity is an important factor that can affect processing characteristics, storage stability, and organoleptic attributes of food and other products. Acidity in aqueous fluids is frequently measured by pH, the negative logarithm of the hydrogen ion concentration.

By increasing the acidity (lowering the pH), or decreasing the acidity (increasing the pH), the taste of products can be affected, the viscosity can be modified, the color and protein stability can be changed. Acids, such as citric, have been added to some moderately acid fruits and vegetables to lower the pH to a value below 4.5 permitting pasturization or sterilization to be achieved under less severe thermal conditions than otherwise necessary. However, the reduced pH often adversely affects the taste of food and the stability, color and physical properties of products.

It has been recognized for a long time that the pH of a solution can be changed by electrodialysis, transfer of hydrogen ions or hydroxyl ions through a porous diaphragm. For example, U.S. Pat. No. 751,179 teaches that hydroxyl ions can be removed from an aqueous sugar solution in an anode compartment by electrodialysis. However, the process forms acids at the anode which must be removed by adding lead saccharate, thereby neutralizing the acid formed.

Three compartment electrodialysis cells with the solution to be treated in the intermediate cell without an electrode avoid the problems of changing the composition of the fluid by oxidation reactions at the anode or reduction reactions at the cathode. However, even when compartments are separated with anion permeable membranes or cation permeable membranes as in U.S. Pat. No. 3,369,906 there is a disadvantage in that ions transferred into the solution from the adjacent compartment are "chemical additives". However, both cation and anion selective membranes may be fouled by ingredients in the product stream. This is particularly true with pulpy products, where particulate deposits can develop on the membrane and reduce the operational efficiency. U.S. Pat. No. 4,317,841 avoids the fouling objection of such classical electrodialysis by contacting a noncathodic extract with chitosan, an amino-bearing polysaccharide derived from bacteria. Such a process while effective for deacidifying coffee is not useful for increasing the acidity (lowering the pH) of a flowable fluid or of a fluid containing suspended matter such as fruit pulp when the pulp is desired in the final product.

One process involving the use of ultrafiltration is disclosed in Blanie et al. U.S. Pat. No. 4,551,341. Blanie et al. is directed to a process for producing clear plant juices in which, following a conventional pressing step, the pulp is separated from a primary juice. The primary juice is then adjusted for pH within a range between 3.5 and 4.0 and for temperature within a range of 50° C. to 65° C. and subjected to ultrafiltration to separate primary juice from pectate raw concentrate. The raw concentrate is then passed to at least a second stage of ultrafiltration. Tubular ultrafiltration membranes are preferred by Blanie et al. to permit a greater linear speed of circulation of fluids and a reduction in the risk of clogging of the membrane. While the process is suitable for preparing clear juices for aseptic packaging but is not suitable for juices or other fluids containing pulp, solids and the like. Further, there is a continued risk of fouling membranes according to the reference.

The prior art processes all have the disadvantage of either being subject to fouling by solids in a flowable fluid or of having a reduced pH which adversely affects product quality.

The present process overcomes the disadvantages of the prior processes by providing a process for reducing the concentration of viable microbial cells in a flowable fluid comprising the steps of:

a. separating the flowable fluid into a sterile serum and a flowable residue containing viable microbial cells and colloids, b. separating serum from step (a) into a first portion of serum and a second portion of serum, c. adjusting the pH of at least part of the second portion of serum by increasing the hydrogen ion concentration therein, thereby reducing the pH, d. combining flowable residue and the second portion of serum from step (c) having a reduced pH to form a combined mixture, e. maintaining combined mixture from step (d) at a sufficient temperature and for a sufficient time to reduce the concentration of viable microbial cells therein, f. adjusting the pH of at least part of the first portion of serum by decreasing the hydrogen ion concentration, thereby increasing the pH, and g. combining serum from step (f) having an increased pH with combined mixture from step (e) to form a flowable fluid with a reduced concentration of viable microbial cells.

Any suitable method may be employed for separating the flowable fluid into a serum and a residue, such as by means of a continuous or batch centrifuge, or by means of membrane technology.

Suitable techniques employing membranes include solution-diffusion processes in which the permeate serum dissolves in the membrane causing swelling and diffuses through the membrane or is transported through a membrane by means of interconnected pores in response to pressure or electrical potential gradients. One skilled in the art will easily select membranes with a molecular cut off point suitable for reducing the concentration of viable cells, colloids and suspended particles according to the size, shape and the properties of the colloids and the viable cells therein as well as the nature of the flowable fluid. A single membrane may be employed or a plurality of membranes, thereby optimizing flow rate of permeate and minimizing fouling of the membrane. The membranes may be hollow fiber membranes, plain membranes or fabricated into a particular shape.

Any convenient method may be employed to increase the pH or decrease the pH of the second and first portion of serum in steps (f) and (c), such as addition of an acid or a base, electrodialysis, Donnan dialysis diffusion of hydrogen ions or hydroxyl ions through cation permeable or anion permeable membranes, electrolysis at an anode to form hydrogen ions or at a cathode to form hydrogen gas and the like. A cation or anion ion exchange polymer may be employed to increase or decrease the pH of the serum.

When the pH of the serum has been increased or decreased by deliberately adding an acid or a base to serum, salts will form which may be undesirable. Such salts may optionally be removed by ion exchange, electrodialysis or other standard methods.

Any flowable fluid may be employed such as a plant juice containing pulp or fibers, a suspension of a pharmaceutically active compound in an aqueous solution or the like.

Bipolar membranes are known to be useful for their ability to rectify alternating current, to improve desalination processes, to act as analogs of certain biological membranes, and to split water in the electrodialysis of acids and bases from salts. Bipolar membranes prepared by various procedures have been reported in the literature. For example, bipolar membranes have been prepared by adhering together two membranes consisting of oppositely charged ion exchange resins in an inert matrix by means of heat and pressure or by means of an adhesive paste (U.S. Pat. No. 2,829,905). Anion and cation exchange membranes have also been fused together by means of heat and pressure to form bipolar membranes as disclosed in U.S. Pat. No. 3,372,101.

A bipolar membrane acts as a barrier to both cations and anions, but when subjected to sufficient electric potential dissociates water into hydrogen ions which are incorporated into the solution on the more electronegative side of the membrane from the cation permeable surface and into hydroxyl ions which are incorporated into the solution on the more electropositive side of the membrane. Therefore, the bipolar membrane does not transport ions from one electrolyte into the solution to be treated, but incorporates either hydrogen ions or hydroxyl ions into the solution to be treated by dissociating the water therein.

The preferred bipolar means for adjusting the pH of the present invention has an advantage over the prior art in that the acidity is adjusted by dissociation of water of the aqueous flowable fluid so that no chemical additives are employed and the chemical composition of flowable fluid is usually exactly the same after treatment as before treatment.

For the purpose of this invention a flowable fluid can be urged to flow through conduit means and can conduct an electrical current, by transfer of ions when subjected to an electric potential gradient, the flowable fluid electrolyte may contain solids, colloids, gases and the like and may have a very high viscosity. A flowable fluid for the purpose of this invention is an aqueous fluid which can be urged to flow through conduits and the like. A flowable fluid may be either an electrolyte or a nonelectrolyte. A flowable fluid may contain solids, such as pulp in a fruit juice, or fibers and cell fragments in tomato paste. Other exemplary flowable fluids include sugar syrups, polymer lattices, aqueous emulsions, mineral slurries and the like.

BRIEF DESCRIPTION OF THE DRAWING

The best mode of practicing the invention will be understood by one skilled in the art by reference to FIG. 1 which exemplifies a process in which the flowable fluid is separated by a membrane into a serum (permeate) and a residue (retentate).

Figure 1:
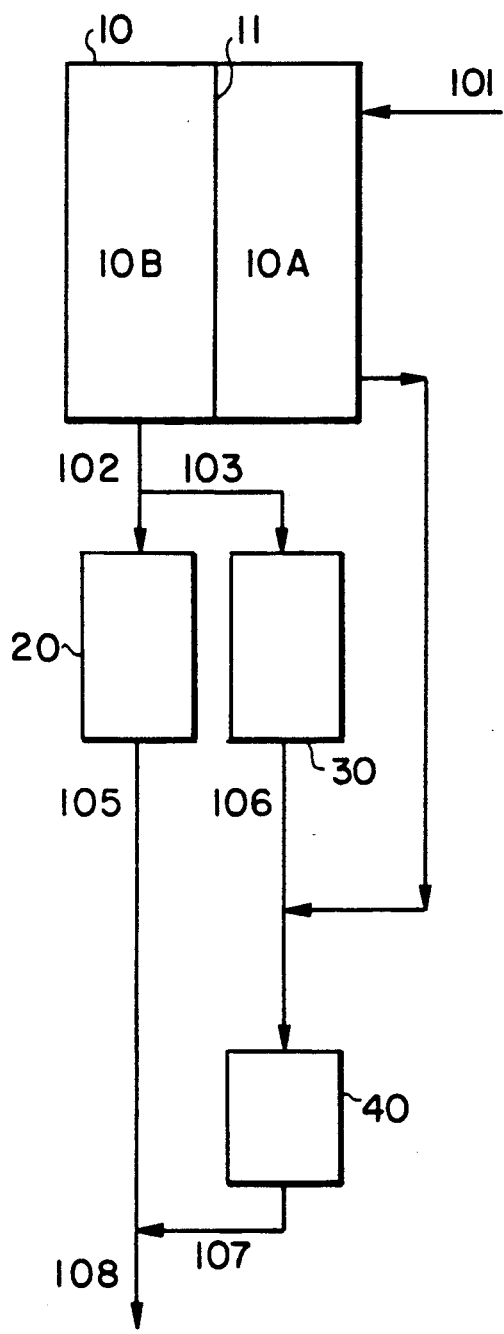
FIG. 1 shows an embodiment of the invention employing module 10 partitioned into two compartments 10A and 10B by membrane 11. Inlet conduit 101 directs flowable fluid from a source (not shown) into compartment 10A. Module 10 is fitted with two effluent conduits, retentate effluent conduit 104 from compartment 10A and permeate effluent conduit 102 from compartment 10B. Conduit 102 connects to manifold 103 which connects to module 20 and module 30. Effluent from module 30 is urged through conduit 106 where it is joined by conduit 104 as inlet means to module 40. Effluent from module 40 is urged through conduit 107 and effluent from module 20 is urged through conduit 105. Conduits 105 and 107 join to form conduit 108 connected to product collection means (not shown).

In operation flowable fluid is urged through conduit 101 into compartment 10A where it is separated by membrane 11 into permeate which is urged into compartment 10B and retentate which is urged into conduit 104. Permeate is urged from compartment 10B through conduit 102 into manifold 103 where it is divided into a first portion urged into module 20 and a second portion urged into module 30. The pH of first portion permeate in module 20 is increased by means therein and concomitantly the pH of second portion permeate in module 30 is reduced by means therein. Effluent from module 30 with reduced pH is urged into conduit 106 where it forms a combined mixture with retentate from conduit 104 and combined mixture is urged into module 40 containing heating means (not shown). Combined mixture is maintained at an elevated temperature in module 40 a sufficient time to reduce the concentration of microbial cells therein and then urged as effluent from module 40 through conduit 107 where it is combined with fluid permeate having an increased pH to form a flowable fluid with a reduced concentration of microbial cells which is urged through conduit means 108 to product collection means.

One skilled in the art will recognize that a plurality of membranes may be employed in module 10 and that permeate from one membrane may be further separated into a second permeate and a second retentate. For example, a flowable fluid may be separated by a first membrane into a first permeate and a first retentate, the first permeate may be separated by a second membrane into a second permeate and a second retentate. The first and second retentate may be combined and treated as the retentate urged through conduit 104, the second retentate may be diverted to another application, or the first retentate may be diverted to another application.

Alternatively, module 10 could represent a centrifuge. In such an embodiment inlet conduit 101 diverts flowable fluid into a centrifuge means 10 separating flowable fluid into serum and residue. Serum is directed from centrifuge 10 through conduit 102 while residue is directed from centrifuge 10 through conduit 104. Subsequently, the serum and residue would be treated similarly to the permeate and retentate above.

I claim:

1. A process for reducing the concentration of viable microbial cells in a flowable fluid comprising the steps of:
   a. separating the flowable fluid into a sterile serum and a flowable residue containing viable microbial cells and colloids,
   b. separating serum from step (a) into a first portion of serum and a second portion of serum, c. adjusting the pH of at least part of the second portion of serum by increasing the hydrogen ion concentration therein, thereby reducing the pH, and decreasing the hydrogen ion concentration of at least part of the first portion of serum, thereby increasing the pH, d. combining flowable residue and the second portion of serum from step (c) having a reduced pH to form a combined mixture, e. maintaining combined mixture from step (d) at a sufficient temperature and for a sufficient time to reduce the concentration of viable microbial cells therein, and f. combining serum having an increased pH with combined mixture from step (e) to form a flowable fluid with a reduced concentration of viable microbial cells.

2. The process of claim 1 wherein a centrifuge is employed for separating flowable fluid into a sterile serum and a residue containing viable microbial cells.

3. The process of claim 1 wherein a membrane is employed for separating flowable fluid into a sterile serum permeate and a retentate residue containing viable microbial cells.

4. The process of claim 1 wherein serum pH is adjusted by electrodialysis.

5. The process of claim 2 wherein serum pH is adjusted by electrodialysis.

6. The process of claim 3 wherein serum pH is adjusted by electrodialysis.

7. The process of claim 4 wherein serum pH is adjusted by Donnan Dialysis.

8. The process of claim 1 wherein serum pH is adjusted by contacting an ion exchange resin.

9. The process of claim 2 wherein serum pH is adjusted by contacting an ion exchange resin.

10. The process of claim 3 wherein serum pH is adjusted by contacting an ion exchange resin.

11. The process of claim 1 wherein the pH is reduced and increased in step (c) by electrodialysis.

12. The process of claim 1 wherein the pH is reduced and increased in step (c) by Donnan dialysis.

13. The process of claim 1 wherein the pH is reduced and increased in step (c) by addition of an acid.

14. The process of claim 1 wherein the pH is reduced and increased in step (c) by electrolysis at an anode to form hydrogen ions.

15. The process of claim 1 wherein the pH is reduced and increased in step (c) by hydrogen ions diffusing through a cation permeable membrane.

16. The process of claim 1 wherein the flowable fluid is a plant juice containing pulp or fibers.

17. The process of claim 1 wherein the flowable fluid is a suspension of a pharmaceutically active compound in an aqueous solution.

18. A process for reducing the concentration of microbial cells in a flowable fluid comprising the steps of:

a. contacting the flowable fluid with at least one membrane which is permeable to the fluid portion of the flowable fluid by impermeable to viable microbial cells thereby separating the flowable fluid into a fluid permeate serum free from viable microbial cells and a flowable retentate residue containing viable microbial cells, b. separating fluid permeate into a first portion and a second portion, c. reducing the pH of at least part of the second portion of fluid permeate, and increasing the pH of at least part of the first portion of fluid permeate, d. combining flowable retentate and fluid permeate from step (c) having a reduced pH to form a combined mixture, e. maintaining combined mixture from step (d) at a sufficient temperature and for a sufficient time to reduce the concentration of microbial cells therein, and f. combining fluid permeate having an increased pH with combined mixture from step (e) to form a flowable fluid with a reduced concentration of microbial cells.

* * * * *